(12) United States Patent
Lee et al.

(10) Patent No.: US 6,723,863 B2
(45) Date of Patent: Apr. 20, 2004

(54) METHODS FOR THE PREPARATION OF PROPYLENE GLYCOL FATTY ACID ESTERS

(75) Inventors: Inmok Lee, Decatur, IL (US); George Poppe, Forsyth, IL (US)

(73) Assignee: Archer-Daniels-Midland Company, Decatur, IL (US)

( * ) Notice: Subject to any disclaimer, the term of this patent is extended or adjusted under 35 U.S.C. 154(b) by 0 days.

(21) Appl. No.: 10/213,434

(22) Filed: Aug. 7, 2002

(65) Prior Publication Data

US 2003/0055208 A1 Mar. 20, 2003

Related U.S. Application Data

(60) Provisional application No. 60/370,728, filed on Apr. 9, 2002, and provisional application No. 60/310,844, filed on Aug. 9, 2001.

(51) Int. Cl.[7] ................................................ C11C 1/00
(52) U.S. Cl. ........................ 554/168; 554/163; 554/169
(58) Field of Search ................................ 554/163, 168, 554/169

(56) References Cited

U.S. PATENT DOCUMENTS

| | | | |
|---|---|---|---|
| 2,197,339 A | 4/1940 | Gooding et al. | |
| 2,197,340 A | 4/1940 | Gooding et al. | |
| 3,083,216 A | 3/1963 | Alsop et al. | |
| 3,669,848 A | 6/1972 | Seiden | |
| 5,491,226 A | 2/1996 | Kenneally | |
| 5,648,483 A | 7/1997 | Granberg et al. | |
| 5,986,117 A | 11/1999 | Cooper | |
| 6,153,773 A | 11/2000 | Kolstad et al. | |

OTHER PUBLICATIONS

International Search Report for International Application No. PCT/US02/25164 mailed on Apr. 21, 2003.

"Sampling and analysis of commercial fats and oils," in *Official Methods and Recommended Practices of the American Oil Chemists Society*, 4th edition, AOCS Official Method Cc 13e–92, Mehlenbacher, V.C., et al., eds., American Oil Chemists Society, Champaign, IL, pp. 1–3 (1990).

Stauffer, C., "Manufacturing Processes for Emulsifiers," in *Bailey's Industrial Oil and Fat Products*, 5th edition, Hui, Y.H., ed., John Wiley & Sons, Inc., New York, NY, pp. 569–601 (1996).

*Primary Examiner*—Deborah Carr
(74) *Attorney, Agent, or Firm*—Sterne, Kessler, Goldstein & Fox, PLLC

(57) ABSTRACT

A process of producing a light-colored, high-monoester mixture from a polyol and an oil is provided wherein the process eliminates the use of organic solvents, multiple water washings and/or molecular distillation. The reactants, a polyol and an oil, described herein, condense in the presence of a catalyst, described herein, at a temperature range from about 180° C. to about 280° C. under an inert atmosphere or the vapor pressure of the polyol with a pressure of about 0 to about 500 psig to yield a monoester mixture possessing a desirable monoester composition and color. The present process yields a final product similar to that of processes which require the use of solvents, multiple water washings and/or molecular distillation.

51 Claims, No Drawings

METHODS FOR THE PREPARATION OF PROPYLENE GLYCOL FATTY ACID ESTERS

CROSS-REFERENCE TO RELATED APPLICATIONS

The present application claims the benefit of the filing date of U.S. Provisional Application No. 60/370,728, filed Apr. 9, 2002, and U.S. Provisional Application No. 60/310,844, filed Aug. 9, 2001, which are incorporated herein by reference in their entireties.

BACKGROUND OF THE INVENTION

1. Field of the Invention

This invention relates to a novel process for producing a monoester mixture which possesses a desirable composition and color.

2. Background Art

In general, the preparation of propylene glycol fatty acid esters is possible from a number of routes. For example, propylene glycol and triglycerides can be reacted together to give a reaction product comprising monoesters of propylene glycol, propylene glycol diesters, monoglycerides, diglycerides, and triglycerides, after removal of the excess propylene glycol and glycerol. A second route is through the reaction of propylene glycol with fatty acids or fatty acid esters, such as methyl or ethyl esters of fatty acids. The product from this reaction will generally be a mixture comprising primarily mono- and diesters of propylene glycol after the removal of water or the low-boiling alcohol (ethanol, methanol, etc.), by-products and any excess starting reactants. A third route is to react propylene oxide with fatty acid, leading to a mixture of monoester isomers. A fourth route is to react propylene glycol with an acid chloride of a fatty acid.

Commercially, propylene glycol monoesters can be prepared by either directly esterifying propylene glycol with fatty acid or by interesterifying triglyceride with propylene glycol. Direct esterification under practical conditions can be accomplished by reacting propylene glycol with a fatty acid to yield approximately 55 to 60 percent of a propylene glycol monoester product; the balance is a reaction by-product comprising diester and unreacted starting material. Because of the high cost of fatty acids relative to triglycerides, the direct esterification process is not commonly utilized. The most commonly utilized process of making propylene glycol monoesters is by interesterifying triglycerides with propylene glycol. This interesterification reaction proceeds at temperatures ranging from 350° to 450° F. with the use of a catalyst such as sodium hydroxide. The resulting crude product contains propylene glycol mono- and diesters, monoglycerides and diglycerides, as well as numerous by-products. The final product composition of these processes can be described in terms of the ratio of mono- to diesters comprising the product. The composition of the end product can be controlled by varying the amounts of polyol with respect to oil, and through manipulating the reaction conditions. A higher concentration of monoesters is usually obtained through a molecular distillation process.

In many instances, it is preferable to utilize a monoester mixture which possesses a high ratio of monoester to diester. A typical commercial operation utilizes a high ratio of propylene glycol to fat to yield a product possessing a high monoester content usually 65% to 75% mono-ester. However, the crude monoester mixtures are typically purified for at least partial isolation of the monoesters from the diesters. Distillation or extraction of the crude monoester mixture produces purified monoester compositions (U.S. Pat. Nos. 3,669,848 and 6,153,773). In general, a distillation process is the most widely used technique for such purification. Typically the crude monoester mixture is distilled under vacuum, in a short path distillation process. The distillate generally comprises greater than 90% (by weight) monoesters. The remaining material generally comprises mainly diesters.

Monoglycerides are mono-fatty acid ester derivatives of the polyol, glycerol. In general, crude monoglyceride mixtures are made from reacting naturally occurring triglycerides, often obtained from oil seed processing, with glycerol. The process is known as glycerolysis. Such reactions generate a mixture of monoglycerides, diglycerides and triglycerides. Limitation on monoglyceride production, via this approach, is generally controlled by: (1) solubility of the glycerol in the reaction mixture; (2) the overall equilibria statistics; and, (3) time. Typical commercially available crude monoglyceride mixtures made using this approach include ratios of monoglyceride:diglyceride:triglyceride (by weight) of about 45:45:10; or about 60:35:5, depending on processing conditions used.

In many instances, it is preferred to utilize more purified monoglycerides. That is, crude monoglyceride compositions or mixtures are purified for at least partial isolation of the monoglycerides from the diglycerides and triglycerides. In general, monoglyceride distillation has been the most widely utilized technique for such purifications. Typically the crude monoglyceride mixture is distilled under vacuum, in a short path distillation process. The distillate generally comprises greater than 90% (by weight) monoglycerides. The remainder generally comprises diglycerides and triglycerides. During the process, the monoglycerides are generally heated to at least 200° C. Sometimes processes which involve distillation of monoesters, such as monoglycerides or propylene glycol monoesters, are associated with the generation of "off tastes" and/or "off aromas" in the final product. The specific source of these off flavors or off aromas is not presently known. However, it seems to be associated with the conduct of distillation processes, i.e., processes that concern heating mixtures containing the monoglyceride (or propylene glycol monoester) of interest until they vaporize under the distillation conditions, typically 240° C.

Typically, the esterification of polyols to produce monoester mixtures is catalyzed by strong base. For example, the most commonly used catalyst is NaOH (Hui Y. H., "Manufacturing Processes for Emulsifiers" in *Bailey's Industrial Oil and Fat Products,* John Wiley & Sons, Inc. (1996), 5$^{th}$ Ed., Vol. 4, pp. 569–601). However, there are reports of monoglyceride production in the absence of catalyst (U.S. Pat. Nos. 3,083,216; 2,197,339 and 2,197,340). These processes either required a distillation or did not produce a high monoester content of about 90%. Alternatively, an acid such as para-toluene sulfonic acid catalyzes the esterification of palmitic acid and propylene glycol (U.S. Pat. No. 3,669,848).

It is also desirable to prepare a monoester mixture of acceptable color. A dark-colored monoester mixture is not suitable for incorporation into products such as paint or food. A Lovibond tintometer is an instrument for evaluating colors on the Lovibond scale, which is a standard scale in the industry. The color of the monoester mixture can be determined by comparing the monoester mixture product to standard reference samples.

It would be useful to develop a process for producing monoesters from polyols and oils in which the product of said process contains a high amount (approximately 90%) of monoester and desirable characteristics such as light color without the need for purification through a distillation or extraction process. It has been found that the novel process disclosed herein yields a monoester mixture composed of about 90% monoester possessing acceptable color as measured by the Lovibond scale. Acceptable color is typically lower than 2 Red on the Lovibond scale.

BRIEF SUMMARY OF THE INVENTION

The present invention is directed to a process of producing a high monoester mixture from a polyol and a triglyceride oil wherein said process eliminates the use of organic solvents, multiple water washings and/or molecular distillation. It has been found that in the presence of a catalyst, described herein, at a temperature range from about 180° C. to about 280° C. under an inert atmosphere or under the vapor pressure of the polyol with a pressure up to about 500 psig at reaction temperature, a polyol, described herein, interesterifies with an oil, described herein, to yield a monoester mixture possessing a desirable monoester composition and color. The present process yields a final product similar to that of processes which require the use of solvents, multiple water washings and/or molecular distillation.

DETAILED DESCRIPTION OF THE INVENTION

In general, the present invention describes a process of preparing a monoester mixture which comprises:

1. A transesterification reaction in the presence of a triglyceride, a polyol and a catalyst, wherein the reaction mixture is heated from about 180° to about 280° C. in the absence of oxygen. It is important to remove oxygen from the reaction environment to prevent deleterious effects of oxidation products on the color of the reaction product. The reaction mixture comprising a triglyceride oil, a polyol and a catalyst is degassed by placing a sufficient vacuum on the reaction vessel to remove dissolved oxygen from the reaction mixture. Once the mixture is degassed and oxygen is removed from the headspace, the reaction proceeds under the vapor pressure of the polyol, and largely in the absence of oxygen. The amount of oxygen present is between about 0 and 160 Torr. Alternatively, oxygen is removed from the reaction vessel by a purge process, and the reaction may then proceed under an inert atmosphere, examples include $N_2$, Ar and $CO_2$ with a pressure of about 0 to about 500 psig. Typically, an amount of a triglyceride oil and a polyol is placed in a reactor vessel in the presence of a catalyst and an inert gas is bubbled through the liquid. The reactor headspace may be purged by evacuating the headspace under vacuum, followed by bubbling of an inert gas to fill the head space. The purge procedure is generally repeated three or four times. After purging, an inert atmosphere with a pressure of about 0 to about 500 psig is left above the liquid. Preferably the inert atmosphere is composed of an inert gas selected from $N_2$, Ar, $CO_2$ and the like. In all embodiments, it is most preferable that the inert gas is $CO_2$. Preferably, the reaction temperature is between about 200° and 260° C., and the pressure is between about 30 and 400 psig. More preferably, the reaction temperature is between about 220° and 240° C., and the pressure is between about 100 and 400 psig. The oil is selected from the group consisting of: vegetable oils, fish oils, animal oils, and transgenically-modified plant oils, and derivatives including hydrogenated oils and mixtures thereof. The triglyceride oils may be saturated, unsaturated, or partially saturated. The vegetable oil may be a vegetable oil which contains conjugated fatty acids. The polyol is selected from dihydroxy polyols which include ethylene glycol, propylene glycol, diethylene glycol, dipropylene glycol and the like. In a preferred embodiment, the oil is a vegetable oil, the polyol is propylene glycol (in any of its optical forms and/or mixtures) and the catalyst is a sodium or potassium salt of a mono- or di-carboxylic acid present in a concentration of between about 0.001% to about 10%. More preferably, the oil is soybean oil, linseed oil, corn oil, sunflower oil, canola oil, rapeseed oil, coconut oil, palm kernel oil, palm oil and hydrogenated derivatives thereof, the polyol is d,l-propylene glycol and the catalyst is a sodium or potassium salt of a monocarboxylic acid present in a concentration of between about 0.001% to about 10%. Most preferably, the oil is soybean oil, the polyol is d,l-propylene glycol and the catalyst is potassium acetate present in a concentration of between about 0.01% to about 1.0%. Preferably, the molar ratio of polyol to oil is about 8:1 to about 14:1. Most preferably, said molar ratio is about 12:1.

2. Neutralizing the reaction by adding a sufficient amount of acid to neutralize the catalyst. Preferably, the acid is phosphoric acid, e.g., 85% phosphoric acid.

3. Separating the excess propylene glycol. The term "separating" comprises useful processes known in the art for segregating components of a mixture as described herein. Such processes are decanting or centrifuging and the like. Typically, decanting comprises adding with mixing about 3% by wt. de-ionized water, allowing the organic and aqueous layers to separate and draining off the excess propylene glycol/glycerol/water layer.

4. Deodorizing the monoester mixture product in a manner known to those skilled in the art at a temperature from about 130°–140° C. The residual propylene glycol and glycerol is removed as the deodorizer distillate (about 15–20% of the product weight).

5. Optionally treating the deodorized monoester mixture product with silica. Preferably, the deodorized product is contacted with about 1% of Trisyl 600 silica at a temperature of about 70° C. to remove residual salts if necessary. Remaining moisture is removed under vacuum at a temperature of about 95° C., and the silica is filtered from the product.

The product of the process of this invention possesses desired characteristics which include typically about 90% monoester content and a light color. Generally, the present process yields a monoester mixture product comprising about 90% monoester content and a Lovibond color of less than 2 Red (American Oil Chemists' Society Official Method cC 13e-92 in *Sampling and Analysis of Commercial Fats and Oils,* pp. 1–3).

In another embodiment, a monoester mixture is produced by agitating a triglyceride oil, a polyol and catalyst to form a mixture, and subjecting the mixture to a vacuum. In this embodiment, a mechanical pump provides a reduced pressure atmosphere in the headspace of the reaction vessel above the mixture. The mixture is heated and agitated under a vacuum. Preferably, the mixture is heated to a temperature from about 5° C. to about 120° C., and the vacuum is from about 1 to about 30 inches of Hg. More preferably, the mixture is heated to a temperature from about 25° C. to about 90° C., and the vacuum is from about 10 to about 30 inches of Hg. The reaction vessel is then sealed by any means capable of closing the reaction vessel from the ambient atmosphere, said reaction vessel is capable of holding a range of pressures. An advantage of this process is that a high-pressure reaction vessel is not required.

The mixture agitating under a vacuum in the sealed reaction vessel is then heated to a temperature of between about 180° C. to about 280° C., wherein a vapor pressure due to the polyol is produced in the headspace of the reaction vessel. More preferably, the temperature is between about 200° C. and 250° C., most preferably about 240° C. The pressure within the reactor is generally from about 0 to about 60 psig, depending on the temperature and the polyol of the mixture.

The triglyceride oil is selected from the group consisting of: vegetable oils, fish oils, animal oils, and transgenically-modified plant oils, and derivatives including hydrogenated oils and mixtures thereof. The triglyceride oils may be saturated (i.e., hydrogenated) or partially saturated. The triglyceride oil may be a vegetable oil which contains conjugated fatty acids. The polyol is selected from dihydroxy polyols which include ethylene glycol, propylene glycol, diethylene glycol, dipropylene glycol and the like. In a preferred embodiment, the oil is a vegetable oil, the polyol is propylene glycol (in any of its optical forms and/or mixtures) and the catalyst is a sodium or potassium salt of a mono- or dicarboxylic acid present in a concentration of between about 0.001% to about 10%. More preferably, the oil is soybean oil, linseed oil, corn oil, sunflower oil, canola oil, rapeseed oil, and hydrogenated derivatives thereof, the polyol is d,l-propylene glycol and the catalyst is a sodium or potassium salt of a monocarboxylic acid present in a concentration of between about 0.001% to about 10%. Most preferably, the oil is soybean oil, the polyol is d,l-propylene glycol and the catalyst is potassium acetate present in a concentration of between about 0.01% to about 1.0%. Preferably, the molar ratio of polyol to oil is about 8:1 to about 14:1. Most preferably, said molar ratio is about 12:1.

The preceding process may further comprise the steps of:
  i. cooling the mixture to a temperature from about 20° C. to about 100° C.,
  ii. neutralizing the catalyst,
  iii. collecting the monoester mixture produced from said mixture, and
  iv. stripping the monoester mixture product at a temperature from about 50° C. to about 150° C., and a pressure from about 0 to about 10 millibars.

Neutralizing the reaction comprises adding a sufficient amount of acid to neutralize the catalyst (to a pH of about 6–7). Preferably, the acid is phosphoric acid, e.g., 85% phosphoric acid.

Collecting the monoester mixture comprises any known methods for separating a multi-phase mixture such as centrifuging and decanting. Decanting comprises allowing phases to separate and draining off the top layer to separate the layer containing the product. The layer containing the product can be stripped of residual polyol and polyol by-products such as glycerol and propylene glycol. As an example, the layer containing the product can be stripped on a wiped-film vacuum stripper at a temperature of about 60° C. to about 100° C., and a pressure of about 1 to 3 millibars (measured after the condenser) to remove glycerol and propylene glycol.

The stripped product is typically low in odor and has a Lovibond color of less than 2 Red.

EXAMPLES

Example 1

In an Autoclave Engineers EZ-Seal 1-Liter autoclave reactor, was placed 350 g, Refined, Bleached and Deodorized (RBD) soy oil (49%) and 363 g anhydrous propylene glycol (51%). To this was added 0.88 g potassium acetate (0.25% on the wt. of soy oil). The reactor headspace was purged 3 times with $CO_2$ at 250 psig $CO_2$ each time. With agitation, the headspace was exchanged 3 more times with $CO_2$ [this time the $CO_2$ being introduced below the liquid surface through the sampling tube]. After these purges, a headspace of atmospheric $CO_2$ (at 0 psig) was left above the liquid. The sealed reactor was heated to 220° C. and the reaction was run at 220° C. for 2 hours at about 60 psig. After cooling, about 1 g. conc. phosphoric acid was added to neutralize the product. About 3% by wt. DI water was added, and the product was allowed to separate into 2 layers. The top layer was collected and deodorized on a lab-scale deodorizer at about 140° C. for a short time to remove residual propylene glycol and glycerol. The deodorized product was very low in odor and had a Lovibond color of 1.9R and 13.0Y. Analysis showed it to be 90.0% monoesters (81.3% propylene glycol monoesters and 8.7% glycerol monoesters), about 6.0% propylene glycol diesters, and 1.3% glycerol diesters. It contained 40 ppm potassium and a 4.9 ppm phosphorus.

Example 2

Silica treatment (using Trisyl® 600) of the product of Example 1 was used to remove the residual salts. After silica treatment, the product contained no potassium or phosphorus. Color was 2.0R and 14.0Y on the Lovibond scale.

Example 3

In an Autoclave Engineers EZ-Seal 1-Liter autoclave reactor, was placed 250 g, RBD soy oil (49%) and 259 g anhydrous propylene glycol (51%). To this was added 0.125 g potassium acetate (0.05% on the wt. of soy oil). The reactor headspace was purged 3 times with $CO_2$ at 250 psig $CO_2$ each time. With agitation, the headspace was exchanged 3 more times with $CO_2$ [this time the $CO_2$ being introduced below the liquid surface through the sampling tube]. After these purges, a headspace of 250 psig atmospheric $CO_2$ was left above the liquid. The sealed reactor was heated to 240° C. and the reaction was run at 240° C. for 2.5 hours at about 400 psig. After cooling and releasing the pressure in the reaction, the pH of the product was adjusted to pH 4 to 5 with phosphoric acid. About 3% DI water was added, and the product was allowed to separate into 2 layers. The top layer was collected and deodorized on a lab-scale deodorizer at between 130° C. and 140° C. for a short time to remove residual propylene glycol and glycerol. The deodorized product was very low in odor and had a Lovibond color of 1.0R and 6.6Y. Analysis showed it to be 90.4% monoesters (79.3% propylene glycol monoesters and 11.1% glycerol monoesters), about 6.0% propylene glycol diesters, and about 0.6% glycerol diesters. The product had an acid value of 1.4 (approximately 0.7% free fatty acids as oleic acid).

Example 4

In an Autoclave Engineers EZ-Seal 1-Liter autoclave reactor, was placed 250 g melted fully hydrogenated (iodine value <2) soybean oil (49%) and 259 g anhydrous propylene glycol (51%). To this was added 0.125 g potassium acetate (0.05% on the wt. of soy oil). The reactor headspace was evacuated under vacuum and then $CO_2$ was bubbled into the liquid of the reactor to 250 psig $CO_2$. The procedure of headspace evacuation with vacuum and then $CO_2$ bubbling was repeated 3 more times. After these purges, a headspace of 250 psig CO$_2$ was left above the liquid. The sealed reactor was heated to 240° C. and the reaction was run at 240° C. for 2.5 hours at about 300 psig. After cooling at about 90° C. and releasing the pressure in the reaction vessel, the pH of the product was adjusted to pH 4 to 5 with phosphoric acid. The product was allowed to separate into 2 layers while warm. The top layer was collected and deodorized at between 120° C. and 135° C. for a short time to remove residual propylene glycol and glycerol. The deodorized product was very low in odor and had a Lovibond color of 0.9R and 2.8Y. Analysis showed it to be 87.0% monoesters (78.4% propylene glycol monoesters and 8.6% glycerol monoesters), about 8.7% propylene glycol diesters, and about 2.5% glycerol diesters. There was about 0.9% glycerine. The product had an acid value of 1.9 (approximately 0.9% free fatty acids as oleic acid).

Example 5

In an Autoclave Engineers EZ-Seal 1-Liter autoclave reactor, was placed 250 g. RBD soy oil (49%) and 259 g. anhydrous propylene glycol (51%). The RBD soy oil had been previously stripped of moisture under vacuum at about 95° C. To the cooled mixture was added 0.125 g. potassium acetate (0.05% on the wt. of soy oil). The reactor headspace was evacuated with a mechanical vacuum pump. The contents of the reactor were then heated from about 28° C. to about 85° C. under vacuum with agitation. When the temperature reached 85–90° C. (after about 10 minutes), the reactor was sealed under a vacuum of about 25 inches of Hg. The sealed reactor was then heated to 240° C. with the pressure increasing to about 25–35 psig at 240° C. The reaction was run with agitation at 240° C. for 2.5 hours at about 25–35 psig. After cooling to about 50° C., conc. phosphoric acid was added to neutralize the product. The product was allowed to separate into 2 layers. The top layer was collected and stripped of glycerol and excess propylene glycol on a wiped-film vacuum stripper at 91° C. and 1.2 to 1.3 millibars of pressure (measured after the condenser). The stripped product was very low in odor and had a Lovibond color of 1.8R and 12.0Y. Analysis showed it to be 80.0% propylene glycol mono-esters, about 7.0% propylene glycol diesters, and about 7.0% monoglycerides. It contained 7 ppm potassium, 15 ppm sodium, and 9 ppm phosphorus.

Having now fully described this invention, it will be understood to those of ordinary skill in the art that the same can be performed within a wide and equivalent range of conditions, formulations, and other parameters without affecting the scope of the invention or any embodiment thereof. All patents, patent applications, and publications cited herein are fully incorporated by reference herein in their entirety.

What is claimed is:

1. A process of producing a monoester mixture comprising reacting a polyol with a triglyceride oil in the presence of a catalyst at a temperature range from about 180° C. to about 280° C. under an inert atmosphere with a pressure from about 0 to about 500 psig wherein a monoester mixture is produced.

2. The process of claim 1, wherein said produced monoester mixture is purified, the process comprising the steps of:
    a) neutralizing said catalyst,
    b) separating excess polyol, and
    c) deodorizing residual product.

3. The process of claim 2, wherein said purification further comprises the treatment of said deodorized residual product to remove salts.

4. The process of claim 1, wherein said triglyceride oil is selected from the group consisting of: vegetable oils, fish oils, animal oils or transgenically-modified plant oils, and derivatives and mixtures thereof.

5. The process of claim 4, wherein said vegetable oils are comprised of soybean oil, linseed oil, sunflower oil, corn oil, canola oil, rapeseed oil, palm kernel oil, cottonseed oil, peanut oil, coconut oil, palm oil, tung oil or safflower oil.

6. The process of claim 1, wherein said triglyceride oil is soybean oil.

7. The process of claim 4, wherein said triglyceride oil is fully hydrogenated.

8. The process of claim 7, wherein said triglyceride oil is a vegetable oil.

9. The process of claim 8, wherein said triglyceride oil is soybean oil.

10. The process of claim 1, wherein said produced monoester mixture has a Lovibond color of less than 2 Red.

11. The process, of claim 1, wherein said catalyst comprises an alkali metal or alkali earth metal salt of a mono- or di-carboxylic acid.

12. The process of claim 1, wherein said catalyst comprises sodium or potassium salt of a mono- or di-carboxylic acid.

13. The process of claim 11, wherein said mono- or di-carboxylic acid is selected from the group consisting of: acetic acid, propionic acid, butyric acid, valeric acid, caproic acid, caprylic acid, capric acid, lauric acid, myristic acid, palmitic acid, stearic acid, eicosanoic acid, oleic acid, linoleic acid, linolenic acid, oxalic acid, malonic acid, succinic acid, glutaric acid, adipic acid, maleic acid and benzoic acid.

14. The process of claim 12, wherein said catalyst is potassium acetate.

15. The process of claim 1, wherein said catalyst is present in a concentration between about 0.001% to about 10%, based on weight amount of the oil in the reaction.

16. The process of claim 15, wherein said concentration is between about 0.01% to about 1.0%.

17. The process of claim 2, wherein said step of neutralizing catalyst comprises adding sufficient amount of an acid to neutralize said catalyst.

18. The process of claim 17, wherein said acid is phosphoric acid.

19. The process of claim 1, wherein said polyol is a dihydric alcohol.

20. The process of claim 19, wherein said dihydric alcohol is propylene glycol.

21. The process of claim 1, wherein the molar ratio of polyol to oil is about 8:1 to about 14:1.

22. The process of claim 21, wherein said molar ratio is about 12:1.

23. The process of claim 1, wherein said temperature range is from about 180° to about 240° C.

24. The process of claim 23, wherein said pressure is from about 30 to about 400 psig.

25. The process of claim 24 wherein, said pressure is from about 100 to about 400 psig.

26. The process of claim 1 wherein said inert atmosphere is selected from the group consisting of N$_2$, CO$_2$ and Ar.

27. The process of claim 1 wherein said inert atmosphere is CO$_2$.

28. A process of producing a monoester mixture comprising,
    a. forming a mixture by agitating a polyol with a triglyceride oil in the presence of a catalyst,
    b. subjecting said mixture to a vacuum, c. sealing reactor and heating the mixture in a vacuum to a temperature from about 180° C. to about 280° C., wherein a vapor pressure is generated, and a monoester mixture is produced.

29. The process of claim 28 further comprising the steps of,
   i. cooling the mixture,
   ii. neutralizing said catalyst,
   iii. collecting the monoester mixture produced from said mixture, and
   iv. stripping the monoester mixture at a temperature from about 50° C. to about 150° C. under vacuum.

30. The process of claim 28, wherein the triglyceride oil is selected from the group consisting of: vegetable oils, fish oils, animal oils or transgenically-modified plant oils, and derivatives and mixtures thereof.

31. The process of claim 30, wherein said vegetable oils are comprised of soybean oil, linseed oil, sunflower oil, corn oil, canola oil, rapeseed oil, palm kernel oil, cottonseed oil, peanut oil, coconut oil, palm oil, tung oil or safflower oil.

32. The process of claim 31, wherein the vegetable oil is soybean oil.

33. The process of claim 28, wherein the triglyceride oil is fully hydrogenated.

34. The process of claim 33, wherein the triglyceride oil is a vegetable oil.

35. The process of claim 34, wherein said vegetable oil is soybean oil.

36. The process of one of claims 10 or 28, wherein said produced monoester mixture has a Lovibond color of less than 2 Red.

37. The process of claim 28, wherein said catalyst comprises an alkali metal or alkali earth metal salt of a mono- or di-carboxylic acid.

38. The process of claim 28, wherein said catalyst comprises sodium or potassium salt of a mono- or di-carboxylic acid.

39. The process of claim 38, wherein said mono- or di-carboxylic acid is selected from the group consisting of: acetic acid, propionic acid, butyric acid, valeric acid, caproic acid, caprylic acid, capric acid, lauric acid, myristic acid, palmitic acid, stearic acid, eicosanoic acid, oleic acid, linoleic acid, linolenic acid, oxalic acid, malonic acid, succinic acid, glutaric acid, adipic acid, maleic acid and benzoic acid.

40. The process of claim 39, wherein said catalyst is potassium acetate.

41. The process of claim 28, wherein said catalyst is present in a concentration between about 0.001% to about 10%, based on weight amount of the oil in the reaction.

42. The process of claim 41, wherein said concentration is between about 0.01% to about 1.0%.

43. The process of claim 29, wherein said step of neutralizing catalyst comprises adding sufficient amount of an acid to neutralize said catalyst.

44. The process of claim 43, wherein said acid is phosphoric acid.

45. The process of claim 28, wherein said polyol is a dihydric alcohol.

46. The process of claim 45, wherein said dihydric alcohol is propylene glycol.

47. The process of claim 28, wherein the molar ratio of polyol to oil is about 8:1 to about 14:1.

48. The process of claim 47, wherein said molar ratio is about 12:1.

49. The process of claim 28, wherein said vacuum is from about 1 to about 30 inches of Hg at a temperature between about 5° C. and about 120° C.

50. The process of claim 28, wherein said vapor pressure is from about 0 to about 60 psig.

51. The process of claim 28, wherein the triglyceride oil is partially hydrogenated.

* * * * *